United States Patent [19]

Namekawa et al.

[11] Patent Number: 4,622,977

[45] Date of Patent: Nov. 18, 1986

[54] ULTRASONIC DIAGNOSTIC APPARATUS

[75] Inventors: Kouroku Namekawa; Akira Koyano; Chihiro Kasai, all of Tokyo, Japan

[73] Assignee: Aloka Co., Ltd., Tokyo, Japan

[21] Appl. No.: 675,824

[22] Filed: Nov. 28, 1984

[30] Foreign Application Priority Data

Dec. 5, 1983 [JP] Japan .............................. 58-228330

[51] Int. Cl.[4] ........................................... A61B 10/00
[52] U.S. Cl. .................................. 128/663; 73/861.25
[58] Field of Search ...................... 73/861.25; 128/663

[56] References Cited

U.S. PATENT DOCUMENTS

| | | | |
|---|---|---|---|
| 4,320,765 | 3/1982 | Cattignol et al. | 128/663 |
| 4,334,543 | 6/1982 | Fehr | 128/663 |
| 4,417,584 | 11/1983 | Cattignol et al. | 128/663 |

OTHER PUBLICATIONS

Brandestini, M. et al, "Topoflow, a Digital Full Range Doppler Velocity Meter", IEEE Trans Sonics & UTS vol. 25, No. 5, Sep. 1978.
Jettnwa, C. P. et al, "Blood Flow Measurements Using Pulsed Random Signal Doppler", IEEE Trans S UIS vol. 22, No. 1, pp. 1-11, Jan. 1975.

*Primary Examiner*—William E. Kamm
*Assistant Examiner*—Francis J. Jaworski
*Attorney, Agent, or Firm*—Koda and Androlia

[57] ABSTRACT

An ultrasonic diagnostic device capable of the accurate real-time measurement and display of the amount of deviation in the velocity distribution of moving objects within a living organism. This apparatus represents an improvement on the ultrasonic diagnostic apparatus of the type wherein an ultrasonic pulse beam is repeatedly transmitted into a living organism at a fixed pulse rate and the reflected echoes are picked up, amplified and displayed, the improvement comprising a complex signal converter for converting a received high frequency signal into complex signals by mixing the received high frequency signal with a pair of complex reference signals which have frequencies that are integer multiples of the pulse rate and which are complexly related to one another, an autocorrelator for determining the autocorrelation of the complex signals, the autocorrelator having a delay time equal to an integer multiple of the pulse period, and a deviation determinator for determining the amount of deviation from the autocorrelation.

2 Claims, 6 Drawing Figures

ULTRASONIC DIAGNOSTIC APPARATUS

BACKGROUND OF THE INVENTION

1. Field of the Invention

This invention relates to an ultrasonic diagnostic apparatus, more particularly to an improved ultrasonic diagnostic apparatus which in addition to velocity information is capable of measuring and displaying the amount of deviation of a signal in respect of the diagnostically useful information of average velocity (also average frequency) of moving objects within a living organism.

2. Description of the Prior Art

The ultrasonic pulse-Doppler method has been practically applied to the measurement of the velocity of movement of a body organ such as the heart, of blood flowing in the blood vessels or of other body fluids. The conventional apparatus for applying this method electrically detects the velocity of movement from the frequency shift of an echo reflected from the moving member within the living body but has been capable of detecting the velocity of movement only at a specific point at a prescribed depth within the organism. Such an ultrasonic pulse-Doppler apparatus of an advanced type for obtaining the velocity distribution of the bloodflow or the like over a wide region has been proposed by the present inventors in Japanese Patent No. 70479/1982 (Publication No. 188433/1983). This apparatus is not, however, able to obtain the velocity deviation distribution. The deviation in the Doppler frequency generally expresses spectral spread. It is a quantity which shows whether the flow of the blood is laminar or turbulent, and the condition of the turbulence. The quantity known as standard deviation value or spread shows the amount of deviation.

SUMMARY OF THE INVENTION

In view of the above-mentioned disadvantages inherent in conventional apparatuses, it is the object of the present invention to provide an improved ultrasonic diagnostic apparatus which is capable of real-time measurement of the deviation along the scanning line of a sent and received ultrasonic pulse beam.

In order to attain this object, the present invention provides an ultrasonic diagnostic apparatus of the type wherein an ultrasonic pulse beam is repeatedly transmitted into a living organism at a fixed pulse rate and the reflected echoes are picked up, amplified and displayed, comprising a complex signal converter for converting a received high frequency signal into complex signals by mixing the received high frequency signal with a pair of complex reference signals which have frequencies that are integer multiples of the pulse rate and which are complexly related to one another, an autocorrelator for determining the autocorrelation of said complex signals and a deviation determinator for determining the amount of deviation from said autocorrelation, whereby the deviation distribution of the velocity of moving objects in the living organism is measured and displayed.

DESCRIPTION OF THE PREFERRED EMBODIMENT

Figure 1:
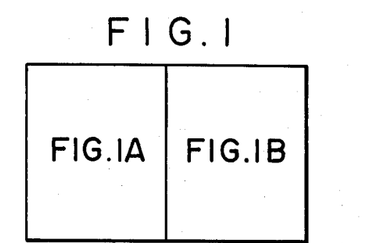
FIG. 1 is a depiction of the relationship of FIGS. 1A and 1B which together form a block circuit diagram of an embodiment of the ultrasonic diagnostic apparatus according to the present invention.
Figure 1A:
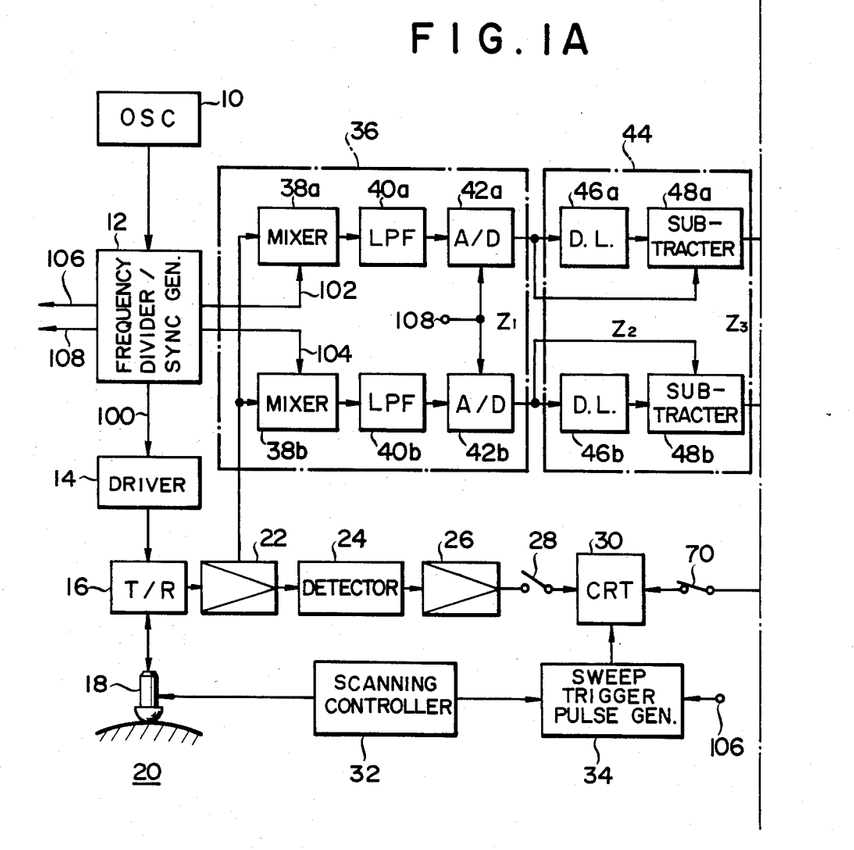
Figure 1B:
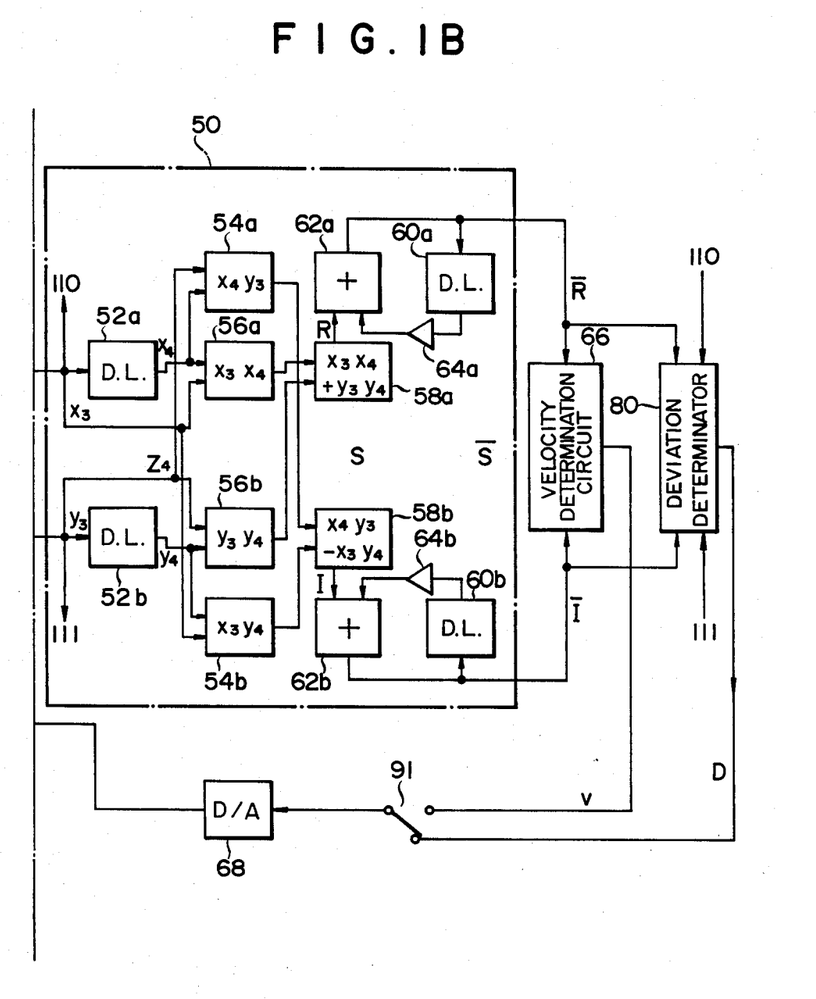

A crystal oscillator 10 produces a stable high frequency signal which is forwarded to a frequency divider and sync generator 12 for producing a number of output signals of desired frequencies. These output signals include a pulse rate signal 100 used for transmission of an ultrasonic pulse beam, complex reference signals 102, 104 for complex conversion, a sweep synchronizing signal 106 for use in displaying the results of the ultrasonic diagnosis, and a clock signal 108 for synchronizing the various sections of the apparatus. In this invention, the complex reference signals 102, 104 are of frequencies which are integer multiples of the pulse rate signal 100 and are phase-shifted from one another, by 90° in this embodiment, so as to be in a complex relationship.

The transmission signal 100 is applied to a probe 18 through a driver 14 and a duplexer 16 and upon being excited by this signal, the probe 18 transmits an ultrasonic pulse beam into a specimen 20.

The echo reflected by the specimen 20 is converted into an electrical signal by the probe 18 and forwarded through the duplexer 16 to a high frequency amplifier 22 by which it is amplified to a prescribed degree and output in two separate directions: to a display section as an ordinary B-mode or M-mode display signal and to an arithmetic processing section provided in accordance with this invention for measuring the amount of deviation of the velocity of movement.

The signal output for carrying out ordinary B-mode or M-mode display is supplied to a cathode ray tube (CRT) display 30 via a detector 24, a video amplifier 26 and a switch 28.

A scanning controller 32 is provided for angularly deflecting the ultrasonic pulse beam from the probe 18, either mechanically or electrically, so as to periodically scan the specimen 20, or for halting the scanning operation at a desired deflection angle. This scanning position signal from the scanning controller 32 and the sweep synchronizing signal 106 from the frequency divider and sync generator 12 are supplied to a sweep trigger pulse generator 34 to sweep-control the CRT display 30.

The other output from the high frequency amplifier 22 is subjected to complex signal processing in accordance with this invention in order to obtain information on the velocity of moving objects. For this purpose, the received high frequency signal from the high frequency amplifier 22 is forwarded to a complex signal converter 36 for conversion into a complex signal.

More specifically, in this embodiment, the complex signal converter 36 comprises a pair of mixers 38a, 38b, each of which includes a phase detector. The received high frequency signal is processed with the complex reference signals 102, 104 in the respective mixers 38 and since the complex reference signals 102, 104 are in a complex relationship, namely since they are 90° out of phase, it is possible to obtain from the mixers 38 complex signal outputs corresponding to the received high frequency signal. More precisely, by means of mixing and detection, each of the mixers 38 outputs two signals, one with a frequency equal to the sum of and the other with a frequency equal to the difference between the frequencies of the received high frequency signal and the complex reference signal. The outputs of the mixers are then forwarded to the low pass filters 40a, 40b which pass only the difference frequency component of each.

Thus, as a result of the mixing and detection operation carried out by the aforesaid mixers 38, the complex reference signals 102, 104 are single-frequency continuous waves, whereas the input signal, namely the received high frequency signal, is a pulse wave including Doppler information. As a result, the outputs from the low pass filters 40 include a large number of spectral components. This complex conversion will now be explained through the use of conversion formulas.

The complex reference signal 102 has a frequency $f_o$ which is an integer multiple of the frequency $f_r$ of the pulse rate signal 100 for the high frequency transmission signal and if the amplitude of this complex reference signal 102 is taken as 1, then it can be represented as the following sine wave voltage signal:

$$\sin 2\pi f_o t \qquad (1)$$

On the other hand, if the transmission frequency is taken as $f_o$, then the high frequency signal received by the probe 18 can be expressed as $$\sin (2\pi f_o t + 2f_d t) \qquad (2)$$

wherein $f_d$ is the Doppler shift frequency.

Although, in general terms, this received signal includes the spectrum
$\sin \{2\pi(f_o \pm nf_r)t + 2f_d(1 \pm nf_r/f_o)t \}$ (wherein $f_r$ is the frequency of the pulse rate signal and n is a natural number such as 0, 1, 2. . . ), in order to simplify the explanation, only the spectrum in the case where $n = 0$ in formula (2) will be considered in the following.

As the product of the complex reference signal 102 and the received high frequency signal is obtained in the mixer 38a, it is possible to derive the output expressed as the following formula which is equal to twice the product of formulas (1) and (2)
$\cos 2\pi f_d t - \cos (4f_o t + 2\pi f_d t)$ Then, since the frequency $2f_o + f_d$ is eliminated from this output by the low pass filter 40a, the output signal becomes $$\cos 2\pi f_d t \qquad (3)$$

On the other hand, since the other complex reference signal 104 is out of phase by 90° with the signal 102, it can be expressed as the following cosine voltage signal $$\cos 2\pi f_o t \qquad (4)$$

and upon being mixed and detected in the mixer 38b and then passed through the filter 40b it is converted to
$$\sin 2\pi f_d t \qquad (5),$$

thus producing a complex signal having a real component as represented by formula (3) and an imaginary component as represented by formula (5). These signals can be expressed by the following complex formula $$Z_1 = \cos 2\pi f_d t + i \sin 2\pi f_d t \qquad (6).$$

The signals $Z_1$ thus obtained by complex conversion are then converted to digital signals by A/D converters 42a, 42b, whereafter they are forwarded to a complex delay-line canceller 44. The clock signal 108 is supplied to the A/D converters 42 where it is used to carry out sampling.

As the embodiment is provided with the complex delay-line canceller 44, it is possible to eliminate the portions of the signal received from the stationary or slow moving members within the living organism and to obtain velocity signals for only the moving portions, thus realizing a great improvement in the quality of the video signal. For example, consider the case of blood flow signals obtained from the living organism. Ordinarily, these signals are contaminated by "clutter," namely echoes from such nearly stationary tissues of the living organism as the walls of the blood vessels and the heart. As this clutter is ordinarily stronger than the blood flow signals, it constitutes a major hindrance to the measurement of the blood flow velocity. In this embodiment, however, since the signals from such low velocity members are eliminated by the complex delay-line canceller 44, it is possible to obtain the signals from the moving members of the living organism uncontaminated by extraneous signals.

The delay-line canceller 44 has a pair of delay lines 46a, 46b each of which has a delay time equal to one period T of the pulse rate signal 100. These delay lines may, for example, be constituted of a number of memories or shift registers equal to the number of clock pulses per one period T. The delay lines 46a, 46b are connected with subtracters 48a, 48b which successively compare the inputs to the delay lines 46a, 46b (i.e. the signals during the current period T) with the outputs thereof (i.e. the signals during the preceding period T) at the same depth and calculate the difference between consecutive periods T. Therefore, since in the case of the echo signals from the stationary and slow moving parts of the living organism there is little or no difference between the current and preceding periods, the output of the subtracters 48a, 48b approaches zero, and, on the other hand, the signals for the high velocity portions, for example the blood flow signals, are obtained as large outputs. Thus, said clutter can be suppressed to a very high degree.

The operation of the complex delay-line canceller 44 will now be explained with reference to the following formulas. Although in the figures digital signals are input to the delay-line canceller 44, for simplicity of explanation, the following discussion will be based on the analog signals represented by formula (6). When the input signals $Z_1$ applied to the delay lines 46 are as represented by formula (6), the output $Z_2$ delayed by one period becomes $$Z_2 = \cos 2\pi f_d(t-T) + i \sin 2\pi f_d(t-T) \qquad (7).$$

As a result, the difference outputs of the subtracters 48 become $$Z_3 = Z_1 - Z_2 = -2 \sin 2\pi^* f_d (T/2) \sin 2\pi f_d \{t-(T/2)\} + i\, 2 \sin 2\pi f_d (T/2) \cos 2\pi f_d \{t - (T/2)\}$$

and if the difference output $Z_3$ is expressed as
$Z_3 = x_3 + iy_3$ then $x_3$, $y_3$ can be obtained as follows $$x_3 = -2 \sin 2\pi f_d (T/2) \sin 2\pi f_d\{t-(T/2)\} \quad (8)$$

$$y_3 = 2 \sin 2\pi f_d(T/2) \cos 2\pi f_d\{t-(T/2)\} \quad (9)$$

Therefore, in accordance with the above, the signals $x_3$, $y_3$ are obtained as outputs from the subtracters 48$a$, 48$b$, respectively.

The complex signals from which the low velocity signal components have been eliminated as described above are then processed by an autocorrelator 50 in order to obtain the autocorrelation of the signals $Z_3$ having a delay of T.

First, the signals $Z_3$ are input to delay lines 52$a$, 52$b$ by which they are delayed by one period to produce signals $Z_4$ as expressed by the following formulas $$Z_4 = x_4 + iy_4$$

$$x_4 = -2 \sin 2\pi f_d (T/2) \sin 2\pi f_d\{t-(3/2T)\} \quad (10)$$

$$y_4 = 2 \sin 2\pi f_d(T/2) \cos 2\pi f_d\{t-(3/2T)\} \quad (11)$$

Then taking $Z_4^* = x_4 - iy_4$, the correlation can be obtained by the following formula $$Zhd\ 3Z_4^* = (x_3+iy_3)(x_4-iy_4) = x_3x_4+y_3y_4+i(x_4y_3-x_3y_4)$$

In order to obtain this correlation, the autocorrelator 50 is provided with four multipliers 54$a$, 54$b$, 56$a$ and 56$b$ and with two adder-subtracters 58$a$, 58$b$.

If the output of the adder-subtracter 58$a$ is taken as R, then from the preceding formulas (8), (9), (10) and (11), we obtain $$R = x_3x_4+y_3y_4 = 4 \sin^2 2\pi f_d(T/2) \cos 2\pi f_d T \quad (12)$$

And if the output of the adder-subtracter 58$b$ is taken as I, we obtain $$I = x_4y_3 - x_3y_4 = 4 \sin^2 2\pi f_d(T/2) \sin 2\pi f_d T \quad (13)$$

Then combining the outputs from the two adder-subtracters, the following is obtained $$S = R\ i\ I \quad (14)$$

Next, as this output S contains the variable signal components and the noise from the apparatus, it is averaged by an averaging circuit for elimination of such extraneous components. The average is expressed by $\overline{S} = \overline{R} + i\overline{I}$, whereby the complex correlation is obtained.

In the averaging circuit, delay lines 60$a$, 60$b$ produce outputs delayed by one period and these outputs are added with the inputs for the current period in the adder-subtracters 62$a$, 62$b$, whereafter the outputs obtained are fed back to the delay lines 60$a$, 60$b$ and the operation is repeated. If a digital circuit is used for this addition, the average value can be obtained merely by outputting the higher order bit of the added output. However, if this operation is simply repeated, the magnitude of the output will successively increase with the increasing number of additions until at last saturation is reached. Because of this, this embodiment is provided with weighting circuits 64$a$, 64$b$ for attenuating the outputs before adding them to the inputs. More specifically, defining the amount of attenuation as $\alpha$, the signal for ten periods earlier, for example, is attenuated by a factor of $\alpha^{10}$ relative to the signal for the current period before being added to the signal for the current period. Thus the fluctuation of the output is made small, so that an averaging effect like that of a low pass filter or a running average circuit can be obtained. Moreover, by changing the amount of weighting by the weighting circuits 64$a$, 64$b$, it is possible to adjust the degree of averaging.

Thus, as described in the foregoing, in this embodiment the correlations of the complex signals are obtained from the autocorrelator 50. These correlation outputs are input to a velocity determination circuit 66 which uses them to obtain the argument $\theta$ of the correlation outputs $\overline{S}$. More specifically, the argument $\theta$ is obtained from the formulas (12) and (13) as follows $$\theta = \tan^{-1}(\overline{I}/\overline{R}) = 2\pi \overline{f_d} T \quad (15).$$

As a result, the Doppler shift frequency $\overline{f_d}$ can be very easily obtained from the argument $\theta$ as follows $$\overline{f_d} = \zeta/2\pi T \quad (16).$$

$\overline{I}\ \overline{R}$ are applied to the deviation determinator 80 of this invention. The operation of this determinator will now be explained.

Figure 2:
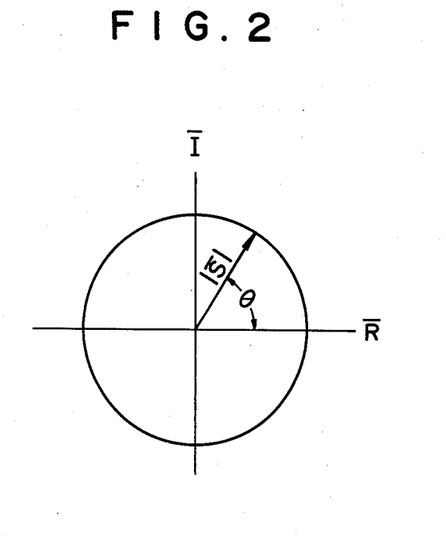
FIG. 2 is a diagram showing the vector of the complex signal.
Figure 3:
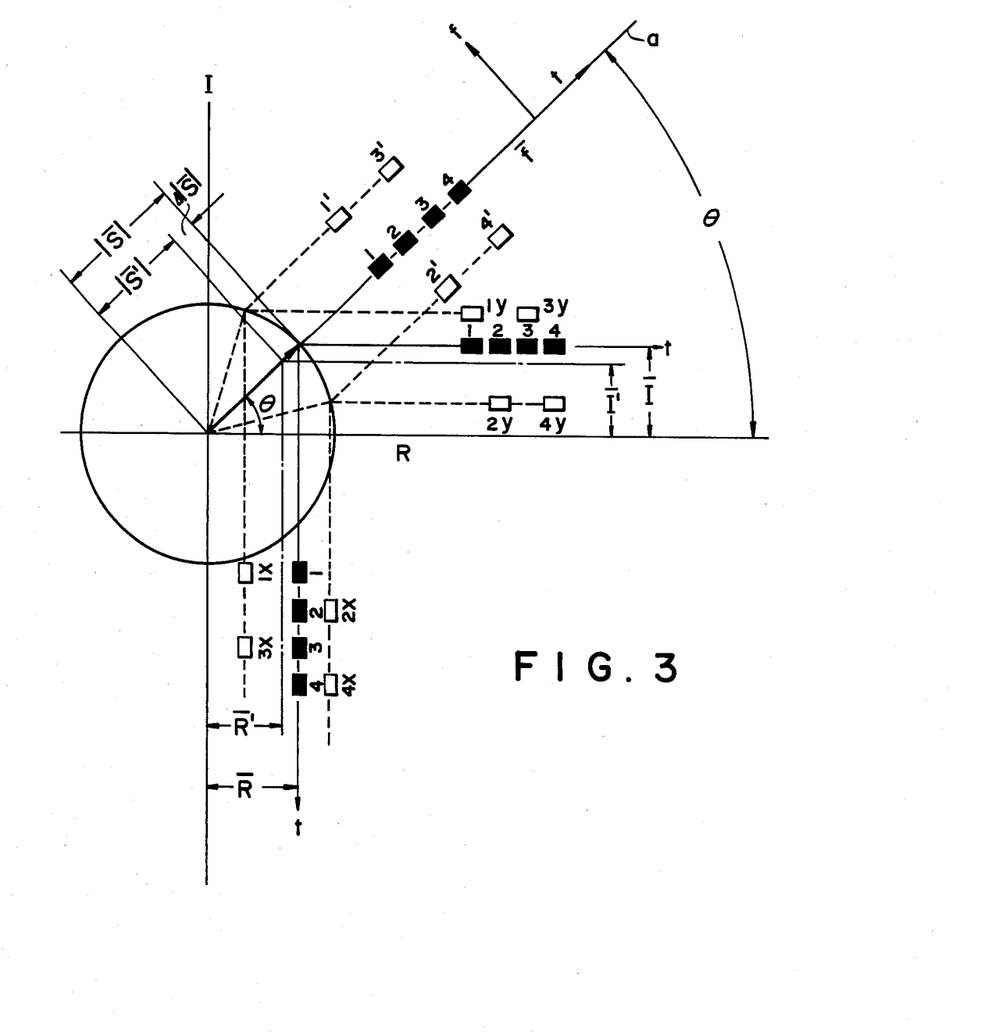
FIG. 3 is a vector diagram illustrating the deviation of the complex signal.

FIG. 2 is a vector diagram showing the relationship between $\overline{I}\ \overline{R}$, and $\theta$. From FIG. 2 the following relationships can be obtained.

$$\overline{R} = |\overline{S}| \cos \theta \quad (17)$$

$$\overline{I} = |\overline{S}| \sin \theta \quad (18)$$

$$|\overline{S}|^2 = \overline{R}^2 + \overline{I}^2 \quad (19)$$

where $|S|$ is an absolute autocorrelation value. Next is an explanation, with reference to FIG. 3, of the difference between when there is no signal fluctuation and when there is signal fluctuation. When there is no signal fluctuation, there is no change in the output from the adder-subtracters 58, this output data S(R, I) appearing in a time order 1, 2, 3, 4, . . . In this case, the average value $\overline{S}(\overline{R}, \overline{I})$ becomes the same as S, the argument at this time being taken as $\theta$. The average frequency of the signal here is $\overline{f}$.

Next, let us consider the case where the complex signal S is fluctuating around the average frequency $\overline{f}$. FIG. 3 shows a case of symmetrical oscillations such as 1', 2', 3', 4' above and below $\overline{f}$, for ease of understanding. In this case, the absolute value of the average $\overline{S}'$ of a complex signal becomes smaller than that where there is no signal fluctuation. The reason for this is that the sum of the complex signals which have various vectors is smaller in amplitude than the sum of those which have the same vectors.

FIG. 3 explains the above relation. In the figure, numerals 1$x$, 2$x$, 3$x$, 4$x$ . . . represent the output of the adder-subtracter 58$a$ and numerals 1$y$, 2$y$, 3$y$, 4$y$ . . . represent the output of the adder-subtracter 58$b$. The fluctuation of these outputs can be decreased by the averaging circuit consisting of the adder 62$a$, 62$b$, the delay line 60$a$, 60$b$ and the weighing circuit 64$a$, 64$b$ for the averaging signals $\overline{R}'$, $\overline{I}'$. In this state, the absolute autocorrelation value $|\overline{S}'|$ becomes smaller than $|\overline{S}|$. And, $\Delta S = |\overline{S}| - |\overline{S}'|$ is the decrease value produced by the signal fluctuation.

Figure 4:
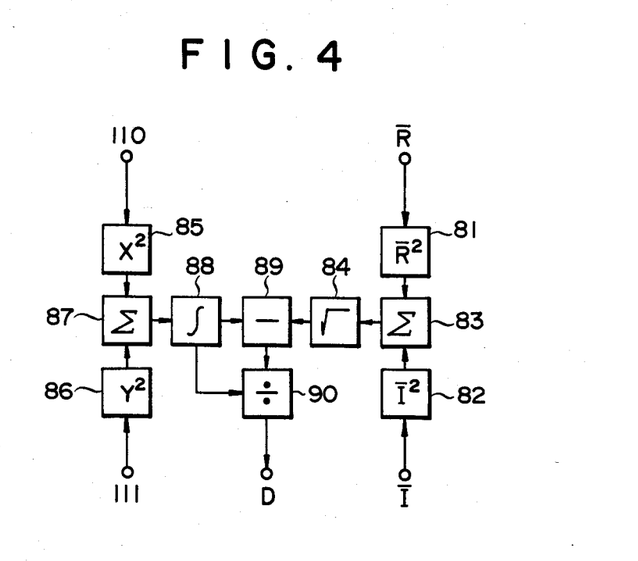
FIG. 4 is a block diagram of the deviation determinator.

FIG. 4 is a block diagram of the deviation determinator 80 which outputs the decrease rate. Inputs $\overline{R}$, $\overline{I}$ are squared by 81, 82 and the square root of the sum is calculated by 83, 84. When there is no deviation, the absolute correlation values are equivalent to the electrical power of the input signal, and will be obtained from 85, 86, 87 as $|S| = x_3^2 + y_3^2$.

This output is taken to an averaging circuit 88 which is similar to the circuit described before (i.e. consisting of adders 62, weighting circuits 64 and delay lines 60), and becomes $|\bar{S}|$. This averaging circuit 88 may be omitted when signal fluctuations are small. The difference between this output and the output of 84 is calculated by 89 to obtain $\Delta S$. The circuit 90 carries out the following computation.

$$\text{ti } D = \Delta S / |\bar{S}| = 1 - (|\bar{S'}|/|\bar{S}|) \tag{20}$$

Equation (20) expresses the ratio of change of the absolute correlation value. Theoretical calculation clarifies that D approximates the spread or variance of a Doppler signal and hence the square root thereof approximates the standard deviation.

With the present invention, in FIG. 4, it is possible to employ a read only memory (ROM) in order to obtain said deviation amount D from $|\bar{S'}|$ and $|\bar{S}|$. In this the ROM is used as a high-speed computing table, where $|\bar{S'}|$ and $|\bar{S}|$ are input and D is the output. This type of computation can also be applied to the various other computation circuits described herein.

The Doppler signal obtained in the manner described above is directed by a switch 91 to a D/A converter 68 and converted to an analog voltage signal which is applied to the CRT display 30 via a switch 70 as a brightness modulation signal, whereby the deviation and velocity distribution of the movement is displayed as a picture on the CRT display 30 in either B-mode or M-mode.

In this embodiment, the CRT display 30 can selectively display either the ordinary video signal received from a video amplifier 26 or the Doppler signal, or can display both of these signals simultaneously. Thus either of the pictures can be displayed independently or they can be displayed one on the other.

Here it should be noted that since the velocity signal is of positive or negative voltage depending on the direction of movement, it is not possible to simultaneously display velocities in both directions using ordinary brightness modulation wherein the brightness of a picture tube is varied using a voltage of only one polarity. Therefore, in this embodiment, a switch is provided in the CRT 30 for reversing the polarity of the input signal, thus making it possible to display velocities in either direction.

Also in accordance with this invention particularly good results can be obtained by employing a color picture tube in the CRT display 30 and displaying movements in different directions in different colors. For example, if positive velocities are displayed in red, negative velocities in blue and reflected echoes from stationary tissues in white, it becomes possible to display the tissue structure of the living organism, the direction of the blood flow and blood flow velocity deviation information all at the same time to thus provide very high-density diagnostic information.

We claim:

1. An improved ultrasonic diagnostic apparatus of the type wherein an ultrasonic pulse beam is repeatedly transmitted by a transmitting means coupled to a transducer means into a living organism at a fixed pulse rate and the reflected echoes are picked up by an echo receiver, amplified by an amplifier means and displayed as the velocity of movement within the organism on a display means, the improvement comprising a complex signal conversion means coupled to an output of the said echo receiver for converting said received reflected echoes into a complex signal, said complex signal converting means comprising means for providing a pair of complex reference signals which have frequencies that are integer multiples of the pulse rate and which are complexly related to one another, mixing means for mixing the received reflected echoes with a pair of complex reference signals, an autocorrelator means coupled to an output of the said signal conversion means for determining the autocorrelation of said complex signal, said autocorrelator means further comprising a time delay means with a time delay equal to an integer multiple of the period of the pulse rate for delaying in time the said complex signal, and a deviation determining means coupled to the output of said autocorrelator means for determining the amount of change in the absolute value of the autocorrelation of said complex signal and for determining the rate of decrease of the absolute value of the said autocorrelation of said complex signal whereby the deviation distribution of the velocity of moving objects in the living organism is measured and displayed.

2. An ultrasonic diagnostic apparatus according to claim 1 further comprising a complex delay-line cancellation means for eliminating the signal components corresponding to slow moving members of the organism from the complex signal.

* * * * *

REEXAMINATION CERTIFICATE (1620th)
United States Patent [19]
Namekawa et al.

[11] B1 4,622,977
[45] Certificate Issued Jan. 7, 1992

[54] ULTRASONIC DIAGNOSTIC APPARATUS

[75] Inventors: Kouroku Namekawa; Akira Koyano; Chihiro Kasai, all of Tokyo, Japan

[73] Assignee: Aloka Co., Ltd., Tokyo, Japan

Reexamination Request:
No. 90/002,337, Apr. 30, 1991

Reexamination Certificate for:
Patent No.: 4,622,977
Issued: Nov. 18, 1986
Appl. No.: 675,824
Filed: Nov. 28, 1984

[30] Foreign Application Priority Data
Dec. 5, 1983 [JP] Japan ............... 58-228330

[51] Int. Cl.⁵ .................................... A61B 8/06
[52] U.S. Cl. ....................... 128/661.09; 73/861.25
[58] Field of Search ............... 128/661.07–661.10; 73/861.25

[56] References Cited
U.S. PATENT DOCUMENTS
4,320,765 3/1982 Cathignol et al. ............ 128/661.09
4,324,258 4/1982 Huebscher et al. ........... 128/661.09
4,573,477 3/1986 Namekawa et al. ........... 128/661.09

FOREIGN PATENT DOCUMENTS
58-63861 4/1983 Japan.

OTHER PUBLICATIONS
Namekawa, K. et al., "Ultrasonic Diagnostic Apparatus", EP0092841 published 02-11-83.
Seo, Y., "Ultrasonic Diagnostic Equipment", EP0081045 published 6-15-83.

Primary Examiner—Francis Jaworski

[57] ABSTRACT

An ultrasonic diagnostic device capable of the accurate real-time measurement and display of the amount of deviation in the velocity distribution of moving objects within a living organism. This apparatus represents an improvement on the ultrasonic diagnostic apparatus of the type wherein an ultrasonic pulse beam is repeatedly transmitted into a living organism at a fixed pulse rate and the reflected echoes are picked up, amplified and displayed, the improvement comprising a complex signal converter for converting a received high frequency signal into complex signals by mixing the received high frequency signal with a pair of complex reference signals which have frequencies that are integer multiples of the pulse rate and which are completely related to one another, an autocorrelator for determining the autocorrelation of the complex signals, the autocorrelator having a delay time equal to an integer multiple of the pulse period, and a deviation determinator for determining the amount of deviation from the autocorrelation.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 2 is confirmed.

* * * * *